(12) United States Patent
Gerber et al.

(10) Patent No.: US 8,282,669 B2
(45) Date of Patent: Oct. 9, 2012

(54) MEDICAL INSTRUMENT FOR GRASPING SURGICAL SUTURE MATERIAL

(75) Inventors: Christian Gerber, Zumikon (CH); Martin Oberlaender, Engen (DE); Sascha Berberich, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 275 days.

(21) Appl. No.: 12/711,794

(22) Filed: Feb. 24, 2010

(65) Prior Publication Data

US 2010/0217286 A1    Aug. 26, 2010

(30) Foreign Application Priority Data

Feb. 24, 2009   (DE) .......................... 10 2009 010 101

(51) Int. Cl.
  *A61B 17/00* (2006.01)
  *A61B 17/04* (2006.01)
(52) U.S. Cl. ...................................... 606/205; 606/148
(58) Field of Classification Search .......... 606/205–207, 606/83, 148, 51, 52; 600/104
See application file for complete search history.

(56) References Cited

U.S. PATENT DOCUMENTS

| | | | |
|---|---|---|---|
| 1,704,992 A | 3/1929 | Sanders | |
| 5,261,917 A | 11/1993 | Hasson et al. | |
| 5,496,335 A * | 3/1996 | Thomason et al. | ........... 606/148 |
| 5,507,756 A | 4/1996 | Hasson | |
| 5,817,111 A | 10/1998 | Riza | |
| 5,951,587 A | 9/1999 | Qureshi et al. | |
| 5,989,277 A * | 11/1999 | LeMaire et al. | ............... 606/205 |
| 6,083,223 A * | 7/2000 | Baker | .............................. 606/52 |
| 6,183,484 B1 | 2/2001 | Matsutani et al. | |
| 6,352,503 B1 * | 3/2002 | Matsui et al. | .................. 600/104 |

FOREIGN PATENT DOCUMENTS

| | | |
|---|---|---|
| DE | 177060 C | 11/1906 |
| DE | 4218191 C1 | 3/1993 |
| DE | 19848958 A1 | 5/1999 |
| EP | 1614391 A1 | 1/2006 |

OTHER PUBLICATIONS

European Search Report; Application No. 10 00 1135; May 20, 2010; 5 pages.
German Search Report; Application No. 10 2009 010 101.2; Oct. 19, 2009; 4 pages.

* cited by examiner

*Primary Examiner* — Julian Woo
(74) *Attorney, Agent, or Firm* — St. Onge Steward Johnston & Reens LLC

(57) ABSTRACT

A medical instrument for grasping surgical suture material, with a shaft on whose proximal end a handle is positioned consisting of at least two gripping members and on whose distal end a tool is positioned consisting of a rigid jaw member and a pivotable jaw member and where the pivotable jaw member can be pivoted with respect to the rigid jaw member for opening and closing with a moveably configured gripping member of the handle, for which purpose the pivotable jaw member and the moveable gripping member are in active connection with one another by means of an actuating element mounted in the shaft. To create a medical instrument that is both easy to operate and makes possible a safe grasping and guiding of the suture material, it is disclosed that in the rigid jaw member there should be configured an indentation that opens toward the pivotable jaw member and that can be covered, with the tool in closed position, only in the center area by the pivotable jaw member.

6 Claims, 5 Drawing Sheets

MEDICAL INSTRUMENT FOR GRASPING SURGICAL SUTURE MATERIAL

CROSS-REFERENCE TO RELATED APPLICATIONS

The present application claims priority of German patent application No. 10 2009 010 101.2 filed on Feb. 24, 2009, the content of which is incorporated herein by reference.

FIELD OF THE INVENTION

The invention relates to a medical instrument for grasping surgical suture material, with a shaft on whose proximal end a handle is positioned consisting of at least two gripping members and on whose distal end a tool is positioned consisting of a rigid jaw member and a pivotable jaw member and where the pivotable jaw member can be pivoted with respect to the rigid jaw member for opening and closing by means of a moveably configured gripping member of the handle, for which purpose the pivotable jaw member and the moveable gripping member are in active connection with one another by means of an actuating element mounted in the shaft.

BACKGROUND OF THE INVENTION

This type of medical suture-grasping instrument is employed in endoscopic surgery in order to allow the surgeon, by grasping the suture material, to produce sutures inside the body. A generic medical instrument is disclosed, for instance, in patent DE 198 48 958 A1. With this known suture-grasping instrument, the rigid jaw member of the tool comprises a recess that runs perpendicularly through the jaw member and that serves for inserting the suture material that is to be grasped with the tool closed. With this known instrument it is possible to catch the suture material well, but the recess configured in the rigid jaw member is too large to be able to guide the suture material precisely to the suturing position that is to be configured.

SUMMARY OF THE INVENTION

Consequently it is the object of this invention to provide a medical instrument for grasping surgical suture material that is both easy to operate and allows secure grasping and guiding of the suture material.

The solution of this object is characterized, according to the invention, in that an indentation is made in the rigid jaw member that is open as far as the pivotable jaw member and that, when the tool is in the closed position, can be covered by the pivotable jaw member only in the central area.

The result of the inventive configuration of the only partly coverable indentation in the rigid jaw member is that the grasped suture material, with the tool closed, is positioned in the indentation of the rigid jaw member to move in a U shape around the pivotable jaw member. The shaped winding of the suture material makes it possible for the suture material to glide through the jaw members when there is a sufficient grip at the same time to allow for precise positioning of the suture material.

The indentation in the rigid jaw member is advantageously configured as a trough that is open exclusively to the pivotable jaw member and is bordered on all sides.

According to an advantageous embodiment of the invention, it is proposed that the pivotable jaw member is tapered in such a way that, with the tool in closed position, the indentation configured in the rigid jaw member is freely accessible on both sides of the pivotable jaw member. As a result of the narrower configuration of the pivotable jaw member in relation to the rigid jaw member, and in particular in relation to the width of the indentation configured in the rigid jaw member, the advantageous U-shaped winding of the grasped suture material around the pivotable jaw member and through the indentation is achieved.

To ensure, in addition, that the suture material can be firmly caught and possibly pulled, it is further proposed with the invention that, in addition to the indentation, a plane surface should be configured on the rigid jaw member, on which surface the pivotable jaw member, with the tool in the closed position, is form-locked together at least in sections. As a result of this inventive configuration of the additional plane clamping surface, the rigid jaw member can be divided into two working areas, namely the area with the indentation for gliding the suture and the area with the plane clamping surface for gripping the suture. The plane surface is preferably configured proximally from the indentation on the rigid jaw member.

According to a first practical embodiment of the invention, it is proposed that the pivotable jaw member of the tool should open in the distal direction so that the inventive instrument with opened jaw member to the front can be conveyed toward the suture material that is to be grasped.

According to an alternative second embodiment of the invention it is proposed that the pivotable jaw member of the tool should open in retrograde direction, that is, with the opening directed to the proximal end of the instrument.

It is further proposed with the invention that the distal end of the rigid jaw member should be configured as a sharp cutting point in order to be able to penetrate through the tissue to be sutured, with the grasped suture material in the closed tool.

It is finally proposed with the invention that a catch hook should be configured on the distal end of the pivotable jaw member pointing toward the rigid jaw member in order to facilitate the gripping and holding of the surgical suture material that is to be grasped with the tool.

Additional properties and advantages of the invention can be seen from the appended illustration, in which one embodiment of an inventive medical instrument for grasping surgical suture material is presented purely as an example, without restricting the invention to this embodiment.

DETAILED DESCRIPTION OF THE INVENTION

Figure 1:
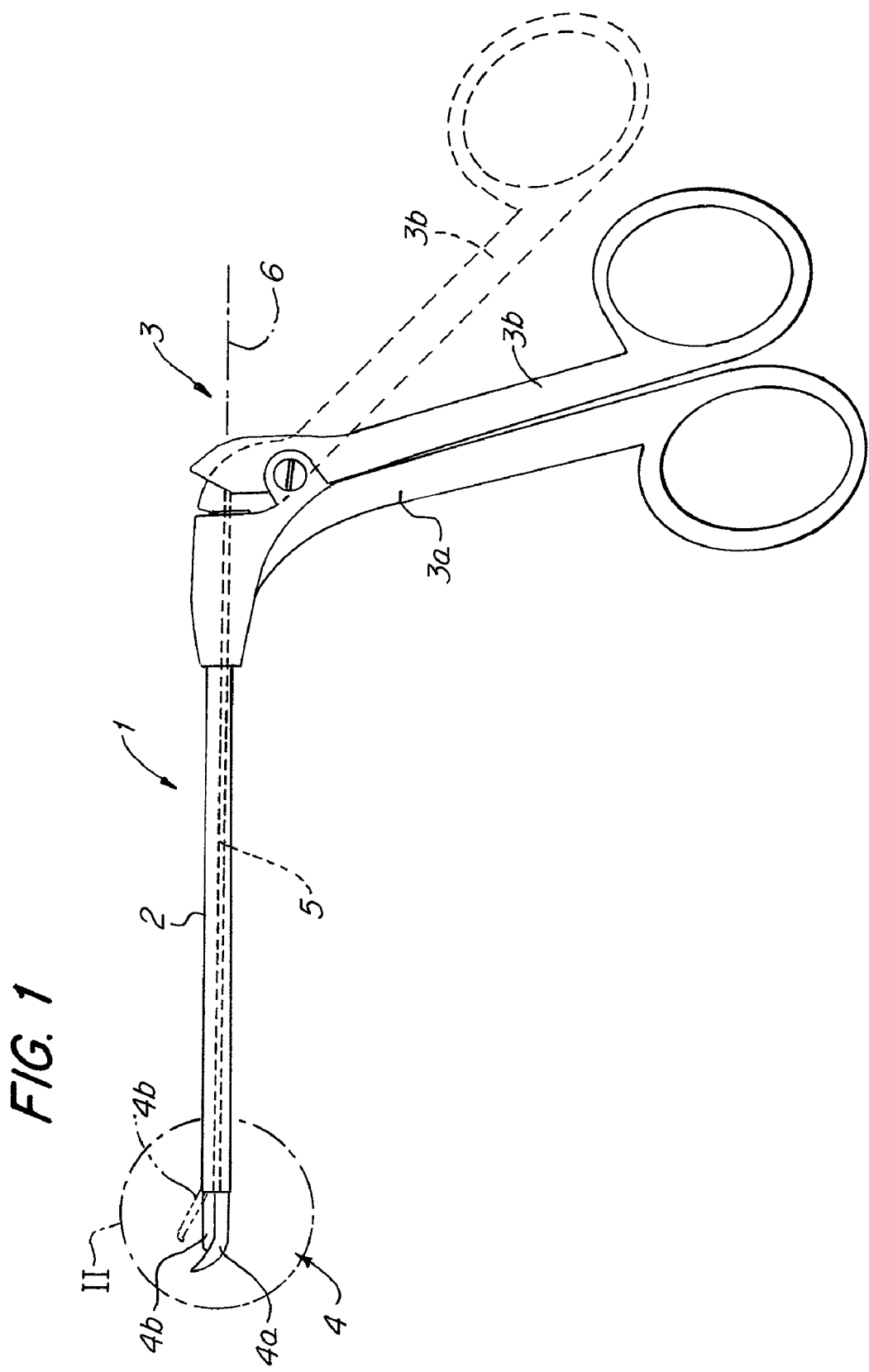
FIG. 1 shows a schematic side view of an inventive medical instrument for grasping surgical suture material.

FIG. 1 shows a medical instrument configured for grasping surgical suture material.

The instrument 1, shown only schematically, consists essentially of a hollow shaft 2, on whose proximal end a handle 3 is position, which consists of a rigid gripping member 3a and a gripping member 3b that can pivot with respect to the rigid gripping member 3a. Positioned on the distal end of the shaft 2 is a tool 4, which consists of one rigid jaw member 4a and one jaw member 4b that can pivot with respect to the rigid jaw member 4a. Which of the two gripping members 3a or 3b of the handle 3 is configured to be pivotable or otherwise movable is irrelevant to the functioning of the medical instrument 1.

As can further be seen from FIG. 1, the pivotable jaw member 4b of the tool 4 and the pivotable gripping member 3b of the handle 3 are in active connection with one another by means of an actuating element 5 that is positioned to slide axially in the hollow shaft 2, in such a way that by displacing the gripping member 3b of the handle, the pivotable jaw member 4b of the tool 4 can be moved from the closed position (shown as shaded in FIGS. 1, 3, and 5 through 7) into the opened position (shown as dotted in FIGS. 1, 2, and 4) or vice versa. The corresponding position of the pivotable gripping member 3b of the handle 3 in each case is likewise shown as shaded (for closed position) and dotted (for opened position) in FIG. 1.

Figure 2:
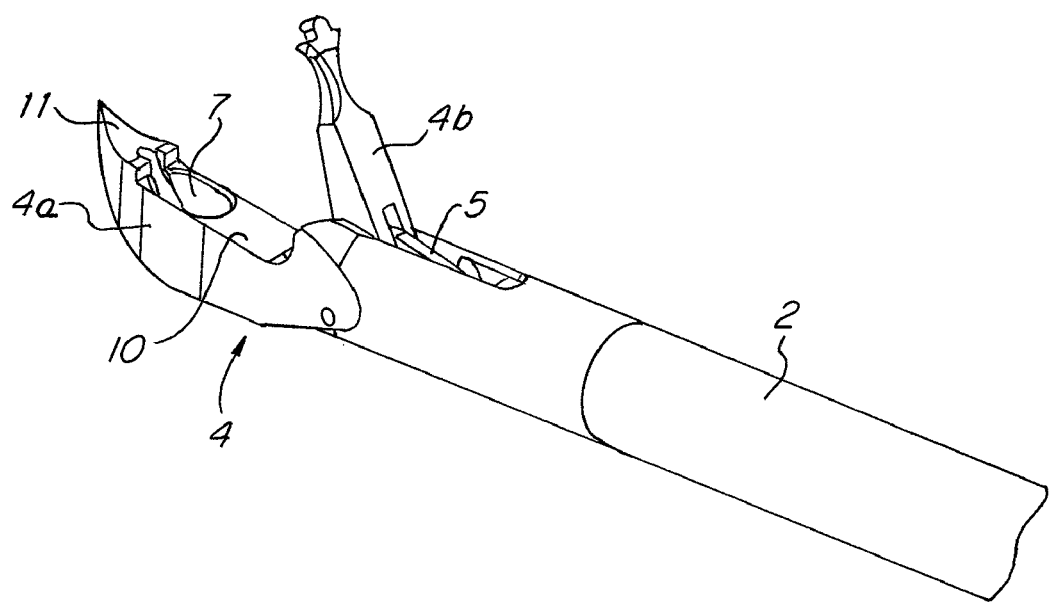
FIG. 2 shows an enlarged perspective view of detail II from FIG. 1, depicting the tool in opened position.
Figure 4:
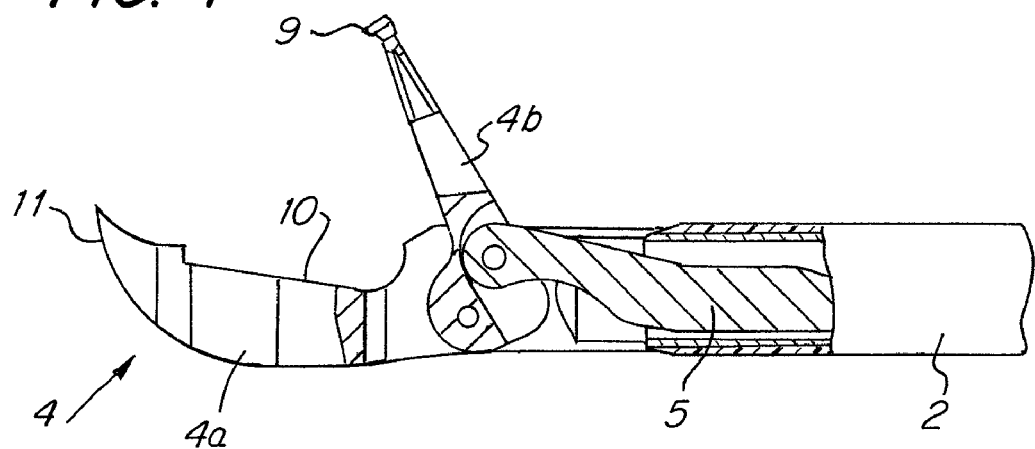
FIG. 4 shows a partly cut-out side view of the depiction from FIG. 2.
Figure 5:
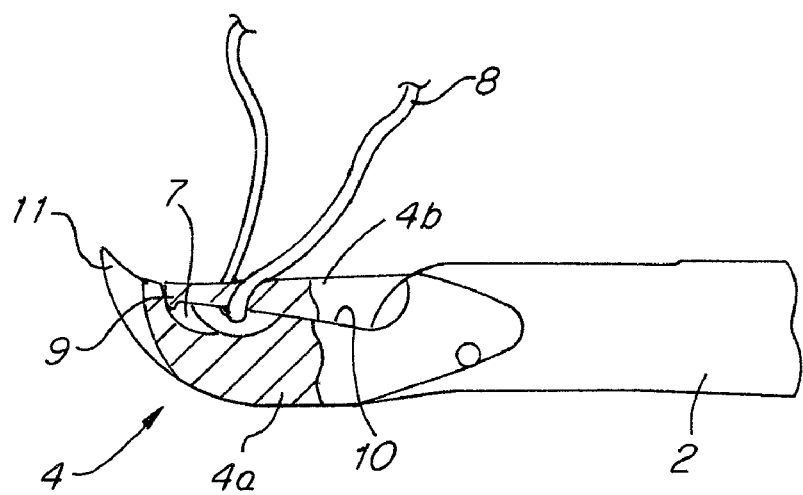
FIG. 5 shows a partly cut-out side view of the depiction from FIG. 3, but with the suture material grasped.
Figure 8:
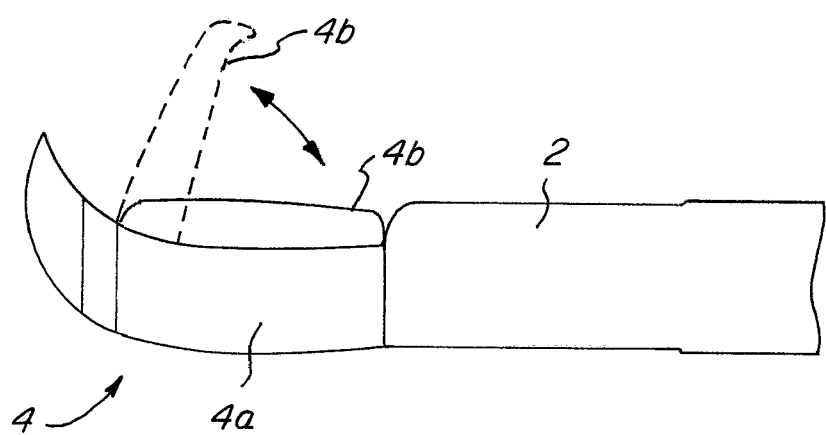
FIG. 8 shows a schematic side view of an inventive medical instrument for grasping surgical suture material, depicting the tool with an opened position in the retrograde direction.

As can further be seen, in particular from FIGS. 2, 4, and 5, the pivotable jaw member 4b of the tool 4 is mounted on the actuating element 5 in such a way that the proximally angled pivotable jaw member 4b opens in the distal direction. Alternatively, it is also possible, of course, to configure the tool 4 in such a way that the pivotable jaw member 4b opens at a retrograde angle in lateral distal direction, that is, with the opening directed toward the proximal end of the medical instrument 1, as can be seen in FIG. 8.

The structure of the jaw members 4a and 4b of the tool 4 can be seen from FIGS. 2 through 7.

In the illustrated embodiment, the tool 4 is configured in such a way that the jaw members 4a and 4b are essentially shown as further extending the instrument's longitudinal axis 6. It is also possible, of course, to configure the tool 4 in such a way that the jaw members 4a and 4b are at an angle to the instrument's longitudinal axis 6. Likewise, contrary to the illustrated straight configuration of the shaft 2, it is also possible to configure the distal end of the shaft 2 as arched.

Figure 3:
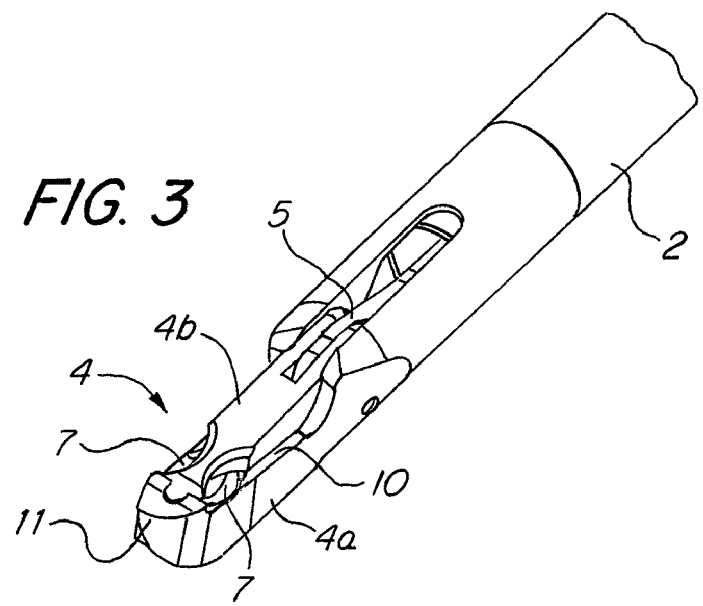
FIG. 3 shows a perspective view according to FIG. 2, but depicting the tool in closed position.

As can be seen in particular from FIGS. 2 and 3, in the rigid jaw member 4a of the tool 4 there is configured an indentation 7 that is open only toward the pivotable jaw member 4b and that, with the tool 4 in closed position (FIG. 3), is covered only in the center area by the pivotable jaw member 4b, so that the indentation 7 remains freely accessible on both sides of the pivotable jaw member 4b also when the tool 4 is in closed position.

In the illustrated embodiment, this only partial covering of the indentation 7 by the pivotable member 4b is achieved as a result of the fact that the pivotable jaw member 4b tapers in the center, that is, with a width that is reduced in the center area. Alternatively it is also possible, for instance, to configure the pivotable jaw member 4b in its entirety as a narrow bridge that can cover the indentation 7 in the rigid jaw member 4a only in the center area.

To facilitate the grasping and holding of a surgical suture material 8 that is to be caught with the tool 4, a catch hook 9 is configured on the distal end of the pivotable jaw member 4b pointing toward the rigid jaw member 4a.

Figure 6:
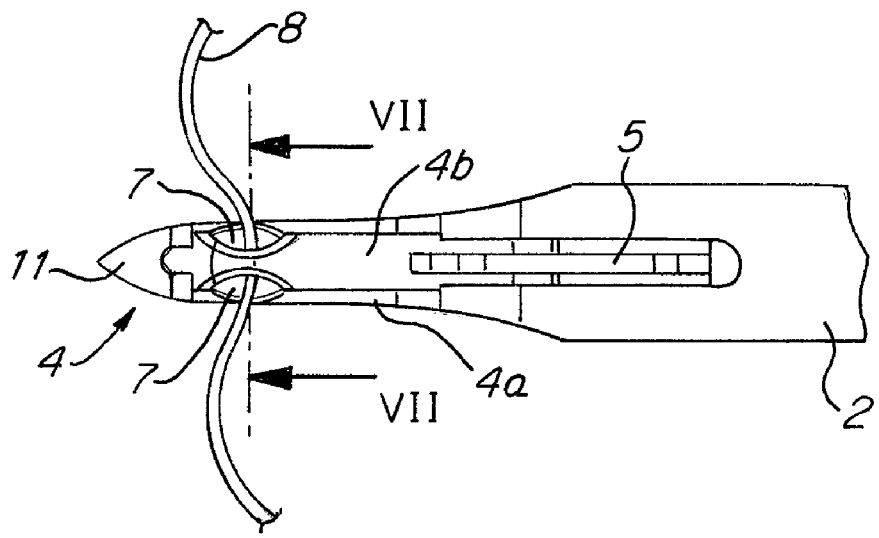
FIG. 6 shows an overhead view of the depiction from FIG. 3, but with the suture material grasped.
Figure 7:
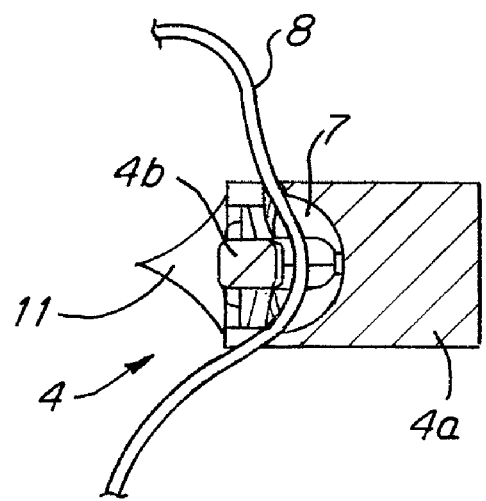
FIG. 7 shows a section along the line VII-VII fro FIG. 6.

The configuration in the rigid jaw member 4a of the indentation that is open only toward the rigid jaw member 4b has the result that the grasped suture material 8, as shown in FIGS. 5, 6, and 7, is pressed inward into the indentation 7 in the rigid jaw member 4a, with the tool 4 in closed position, and is positioned in a U-shape winding around the pivotable jaw member 4b in the indentation 7 of the rigid jaw member 4a.

This U-shaped winding of the suture material 8 makes possible the continued gliding of the suture material 8 through the jaw members 4a, 4b, but with sufficient grip, at the same time, to be able to position the suture material 8 precisely.

In the illustrated embodiment of the medical instrument 1, the holding and guiding of the suture material 8 gripped by the tool 4 can be improved if, on the rigid jaw member 4a of the tool 4, in addition to the indentation 7 a plane surface 10 is configured on which the pivotable jaw member 4b that clamps and grasps the suture material, with the tool 4 in closed position, is form-fitting, at least in sections, as can be seen from FIG. 5.

Because of this configuration of the additional plane clamping surface 10, the rigid jaw member 4a can be divided into two working areas, namely one area equipped with the indentation 7 for guiding the suture material and one area equipped with the plane surface 10. The plane surface is preferably configured proximally from the indentation 7 on the rigid jaw member 4a.

As can be further seen from FIGS. 2 through 7, the distal end of the rigid jaw member 4a is configured as a sharp cutting point 11 to permit penetration of the tissue that is to be sutured, with the grasped suture material 8, when the tool 4 is in closed position.

A medical instrument 1 of this configuration for grasping surgical suture material 8 is distinguished by the fact that the grasped suture material 8 is conducted in a U shape around the pivotable jaw member 4b in such a manner as to allow secure grasping and conducting of the suture material 8.

What is claimed is:

1. A medical instrument for grasping surgical suture material, with a shaft on whose proximal end a handle is configured that consists of at least two gripping members and on whose distal end a tool is positioned consisting of a rigid jaw member and a pivotable jaw member and where the pivotable jaw member can be pivoted with respect to the rigid jaw member for opening and closing by means of a displaceable configured gripping member of the handle, for which purpose the pivotable jaw member and the displaceable gripping member are in active relation with one another by means of an actuation element mounted in the shaft, characterized in that there is configured in the rigid jaw member an indentation that is configured as a trough that is open exclusively towards the pivotable jaw member and is bordered on all sides and that, with the tool in closed position, can be covered only in a center area by the pivotable jaw member and wherein the pivotable jaw member has a tapered configuration in such a way that, with the tool in the closed position, the indentation configured in the rigid jaw member is freely accessible on both sides of the pivotable jaw member and in that in the closed position, the tool is configured to press the grasped suture material inward into the indentation in the rigid jaw member by the pivotable jaw member, wherein in addition to the indentation on the rigid jaw member, a plane surface is configured on which the pivotable jaw member, with the tool in the closed position, is form-fitting at least in sections of the plane surface.

2. A medical instrument according to claim 1, wherein the plane surface is configured proximally from the indentation on the rigid jaw member.

3. A medical instrument according to claim 1, wherein the pivotable jaw member of the tool opens in the distal direction.

4. A medical instrument according to claim 1, wherein the pivotable jaw member of the tool opens in retrograde direction.

5. A medical instrument according to claim 1, wherein the distal end of the rigid jaw member is configured as a sharp cutting point.

6. A medical instrument according to claim 1, wherein a catch hook pointing toward the rigid jaw member is configured on the distal end of the pivotable jaw member.

* * * * *